United States Patent [19]

Stoy

[11] 4,110,529

[45] Aug. 29, 1978

[54] METHOD OF MANUFACTURING SPHERICAL POLYMER PARTICLES FROM POLYMER SOLUTIONS

[75] Inventor: Vladimir Stoy, Prague, Czechoslovakia

[73] Assignee: Ceschoslovak akademie ved, Prague, Czechoslovakia

[21] Appl. No.: 633,787

[22] Filed: Nov. 20, 1975

[30] Foreign Application Priority Data

Nov. 26, 1974 [CS] Czechoslovakia .................. 8071/74

[51] Int. Cl.² ............................ C08J 3/16; C08J 9/28
[52] U.S. Cl. .................................. 528/491; 106/122; 106/198; 528/492; 528/493; 528/494; 528/495; 528/496; 528/497; 528/498; 528/499; 528/502; 521/64
[58] Field of Search ................ 260/34.2, 2.5 B, 2.5 A, 260/2 R, 2 EP, 75 T; 106/198, 122; 528/491, 492, 493, 494, 495, 496, 497, 498, 499, 502

[56] References Cited

U.S. PATENT DOCUMENTS

| | | | |
|---|---|---|---|
| 2,722,528 | 11/1955 | Johnson | 106/198 |
| 2,740,723 | 4/1956 | Voris | 106/198 |
| 2,814,570 | 11/1957 | Sloan | 106/198 |
| 3,669,922 | 6/1972 | Bartsh et al. | 260/34.2 |
| 3,737,401 | 6/1973 | Tsou et al. | 260/34.2 |
| 3,847,886 | 11/1974 | Blunt | 528/491 |
| 3,923,707 | 12/1975 | Berg et al. | 260/34.2 |
| 3,945,978 | 3/1976 | Berg et al. | 260/34.2 |

*Primary Examiner*—Allan Lieberman

[57] ABSTRACT

The invention relates to a method of manufacturing spherical particles, either homogeneous or porous, from polymer solutions, wherein a polymer solution is dispersed or suspended in a liquid dispersing medium incapable of dissolving the polymer and immiscible with the polymer solvent, and the emulsion thus obtained is poured, while stirring, into an excess of a polymer-coagulating liquid which is miscible with the polymer solvent but immiscible with the dispersing medium, whereafter the two liquid phases are separated from each other and from the spherical polymer particles which are then isolated.

12 Claims, No Drawings

METHOD OF MANUFACTURING SPHERICAL POLYMER PARTICLES FROM POLYMER SOLUTIONS

BACKGROUND OF THE INVENTION

Polymers in the form of small spherical particles are useful for many industrial applications such as for easy metering and filling of molds and extruders, for the manufacture of ion exchangers, sorbents, molecular sieves, carriers of catalysts etc. Small spheres or beads of polymers are usually made by polymerization or copolymerization in suspension. This method cannot be used, however, in the case of ready-made or natural polymers and their derivatives.

Suspension polymerization has, in cases where it can be used at all, several inconveniences. The size of the particles increases with increasing degree of polymerization and is not easily controllable. At high conversions the viscosity rises so that the particles become sticky, agglomerate and separate from the dispersing medium. Therefore "stabilizers" of suspension are often added, contaminating the product and raising the production cost. When manufacturing copolymers, neither any of the monomers nor the copolymer must be soluble in the dispersing medium: This condition cannot be always easily realized, having regard to the different characteristics of the monomers. This problem is further complicated if various additives are to be used such as dyestuffs, foaming agents or biologically active substances. Another disadvantage of suspension polymerization is its long duration and high energy requirement.

It is known e.g. from the U.S. Patent Specification No. 3,597,350 (Determann et al) to prepare cellulose in spherical form by dispersing viscose in an organic solvent, adding a detergent, and also adding an acid which is soluble in the dispersing phase. A suitable acid is e.g. benzonic acid. Alternatively the viscose suspension is poured into a solution of benzoic acid. in benzene. In this case, the coagulating agent is dissolved in a solvent miscible with the dispersing medium and the coagulation is a chemical process - decomposition of cellulose xanthogenate.

According to another method a suspension of viscose in a mineral oil is gelled by heating, and regeneration of cellulose in bead form is carried out by adding an oil-soluble acid, preferably acetic acid. (Peska et al, Czechoslovak Pat. Appln. No. PV 3858-74).

Still another method of preparing spherical particles from film waste from cellulose acetate or acetobutyrate consists of suspending solutions of said waste in organic volatile solvents immiscible with water in an aqueous solution of an emulsifier. The aqueous solution is heated to the boiling point of the organic solvent which is distilled off. Here the coagulation is brought about by removing the solvent preventing the polymer from contact with water in which the polymer is not soluble. (Czechoslovak Pat. No. 109217, Sramek et al). This method is requires considerable energy and is time concuming; It cannot be used generally.

GENERAL DISCLOSURE

It has been found now that spherical particles or beads of various polymers can be easily and economically manufactured by dispersing a solution of the polymer, containing, if desired, various additives, in a liquid dispersing medium immiscible with any component of the polymer solution, and by stirring the emulsion into an excess of a liquid which coagulates the polymer, dissolves its solvent but is immiscible with the dispersing medium. The two liquid phases are then separated from each other and from the polymer beads which are isolated.

The size of the beads can be varied by regulating the intensity of stirring, the viscosity of the polymer solution as well as that of the dispersing medium, the volume ratio of the two phases, the interphase tension, the polymer concentration and the intensity of coagulation. The main advantages of the new process in comparison with suspension polymerization are the following:

(i) The viscosity of the dispersed phase remains constant and the size of the beads can be more easily controlled, even if no "stabilizers of suspension" are added.

(ii) The new process is not time-consuming and thus does not require much energy.

(iii) The new process is more suitable for manufacturing polymer beads containing liquid or solid additives in the form of a solid solution or dispersion, owing to the absence of highly reactive compounds such as free radical-liberating and strongly oxidizing polymerization catalysts and unsaturated monomers. On the other hand, the additives are in contact with the inert polymer only, while in suspension polymerization they could adversely affect the polymerization process. It is therefore, possible, in the process according to the invention, to utilize considerably more of additives such as dyestuffs, pigments, greases, plasticizers, surface-active substances, antistatics, fillers, sorbents, catalysts, reactive agents, perfumes, drugs, biologically active substances, radiation-absorbing compounds, antioxidants, and similar additives.

The polymer solution for the process of the invention can be prepared by dissolving a polymer in an appropriate solvent, or also by polymerization in solution. As the present process is of merely physical nature, any soluble polymer or copolymer can be used as starting material, provided that the dissolution as well as the coagulation necessitate no chemical transformation of the polymer. Thus, it would be superfluous to list all usable addition- and condensation polymers made, e.g., from vinyl and acrylic esters and ethers, or other esters of unsaturated acids and alcohols such as polyacetals, polyamides, polyesters, polyurethanes, polysiloxanes, polyoxiranes, polydienes etc. since no polymer which is physically soluble as such can be excluded.

As solvent for the polymer, any liquid, organic or inorganic, dissolving it without permanent chemical transformation can be used. The choice of solvents is very broad and includes not only all known polar liquids such as water, dimethyl formamide, dimethyl sulfoxide, strong inorganic acids etc., as well as non-polar or low-polar solvents such as aromatic hydrocarbons, ethers, alcohols, hydroaromatic compounds etc., but also less usual substances such as organic acids and their esters, nitriles lactams and anhydrides, liquid ammonia, aqueous solutions of salts such as zinc chloride, sodium, calcium or lithium rhodanide, lithium bromide, phenols, ketones, organic bases such as pyridine and its derivatives, glycols and other polyols, organic halogen- and nitro compounds etc., and mixtures thereof, briefly all solvents causing no permanent chemical transformations of the polymer in question.

As dispersing medium any liquid with a considerably different density of cohesion energy in comparison with the polymer and the polymer solvent can be used, immiscible with both of them. Usually, the dispersing medium consists of liquids with a very low density of cohesion energy such as aliphatic, aromatic or hydroaromatic hydrocarbons and their halogen derivatives, low-molecular polysiloxanes, olefins, ethers and similar, or, on the contrary, such with a very high cohesion energy density such as water and aqueous solutions of organic and inorganic acids, bases and salts, anhydrous acids, lactams, pyridine, ethylene glycol, glycerol and other polyols, dimethyl formamide, dimethyl sulfoxide etc. The viscosity of the dispersing medium can be, if desired, increased in known manner by dissolving therein suitable high-molecular polymers such as various sorts of rubber, atactic polypropylene, polyisobutylene, polyvinyl acetate, polyvinyl alcohol, polyethylene oxide, gelatin, starch etc.

As known from the theory of dispersions, the viscosity of the dispersing medium must not be much lower than that of the dispersed phase, since the energy necessary for splitting the droplets of the dispersed phase is transmitted from the stirrer through the dispersing medium. With a decreasing ratio of viscosities of the two phases the size of the droplets increases, and if the difference of viscosities is about one order, the droplets are not formed at all. In usual processes for manufacturing spherical particles such as in suspension polymerization or in cooling a melted polymer, or in cooling a highly concentrated hot polymer solution, it is necessary to adjust the viscosity of the dispersing phase to a value which is satisfactory in the critical period, when the viscosity of the dispersed phase is already high and the droplets are still sticky and the fraction of inelastic collisions of the droplets is still high. Thus, the optimum setting is possible in a certain time interval only, not during the process as a whole. In the present process, however, it is sufficient to adjust the viscosity of the dispersing phase to that of the dispersed phase at the start only, since a non-sticky skin is formed on the surface of the droplets at the very beginning of the coagulation, whereby the fraction of elastic collisions is strongly increased. In contradistinction to known processes, there is no danger of dividing the dispersion into two continuous phases.

If desirable, the interphase tension can be also varied by adding either surface-active substances or finely powdered solids in order to control the particle size.

The volume ratio of dispersed to dispersing phase can vary from 1:1 to 30:1, preferably from 2:1 to 15:1.

The coagulating liquid is miscible with the polymer solvent only, immiscible with the dispersing medium and, naturally, not dissolving the polymer. The choice of coagulating liquid is very broad again, as it is usually easy to find at least one suitable combination of the three liquids, namely of the solvent, dispersing medium and coagulant.

By choosing properly the conditions at the coagulation and the intensity of the latter, it is possible to obtain any desired degree of porosity within rather broad limits. At high coagulating rate, i.e. at a large surplus of the coagulant which is effective already in the presence of a high fraction of the solvent and which can diffuse easily into the swelled polymer, being easily miscible with its solvent, there are obtained porous beads the size of which is substantially equal with that of the droplet of polymer solution from which the bead was formed. The intensity of coagulation can be further increased by increasing the temperature. In this way, spherical polymeric particles with high porosity and large inner surface are obtained.

By lowering the intensity of coagulation the porosity can be gradually dimished up to the limit situation where the loss of the solvent in the peripheral region of the droplet is continuously replaced by diffusion of the solvent from the interior; In this case, non-porous beads are obtained. The coagulation intensity can be lowered e.g. by lowering the temperature, or by using a milder coagulant in smaller surplus, or by using a mixture of a coagulant with a solvent, the concentration of the coagulant being increased during the process. If the polymer solvent is either acid or basic, the coagulation can be, if desired, accompanied by neutralization.

The immiscibility of the coagulating liquid with the dispersion medium has the advantage that the two phases can be easily separated and that the suspended droplets are protected from sticking together in the critical first period by the dispersing medium. It is surprising, however, that the coagulation step cannot be reversed by pouring the coagulating liquid into the emulsion of the polymer solution; Satisfactory results are obtained only if the emulsion is poured into an excess of the coagulant.

The porosity of the beads and particularly their volume can be further increased by using a volatile polymer solvent and by carrying out the coagulation at temperatures above the boiling point of the solvent, stirring the emulsion into a heated coagulating liquid.

The process of the invention makes it possible to use still other methods of imparting porosity of a polymer, e.g. the known method of "lost crystals". A powdered solid, e.g. in the form of small crystals, can be added to the polymer solution in which it is insoluble. The solid particles are washed out of the beads either by the coagulant or afterwards by an approriate solvent. Particularly fined particles are obtained if the solid is coagulated simultaneously with the polymer. Similarly, it is possible to admix with the polymer solution fine droplets of a liquid or of a melt immiscible with both the solvent and the dispersing medium; the admixed liquid is either eluted or evaporated from the coagulating or coagulated beads. Particularly fine pores are obtained if there is dissolved in the polymer solution a liquid substance which is coagulated simultaneously with the polymer in which it is insoluble.

PREFERRED EMBODIMENTS

The method of the invention is advantageous, making possible the manufacture of spherical polymer particles in a broad range of size and porosity degree, with closed or open pores taking up to 95% of the particle volume or even more. Moreover, the size of the pores and thus the inner surface of the particles can be varied within broad limits.

Effective stirring during the coagulation step is highly desirable, otherwise the coagulation takes place on that part of the particle surface only which is in contact with the coagulant on the interface between the coagulant and the dispersing medium. The particles are then deformed. It is therefore advisable to disintegrate the dispersing medium into droplets not too much larger than those of the polymer solution. The size of the dispersed or suspended droplets of the polymer solution is thereby influenced but slightly. If the stirring is omitted so that the droplets of the polymer solution freely sediment on the interface between the dispersing medium and the coagulating liquid, the coagulated polymer particles take the shape of regular small discs or saucers.

Another advantage of the new process is the possibility to incorporate an unusually large amount of useful additives into the porous beads, often more than ten times the weight of the polymer itself. The beads the pores of which are filled with the additives do not loose their cohesion. Thus, the beads can be used as storechambers for various substances such as drugs, catalysts, biologically active substances, dyestuffs, syrups, perfumes, concentrates of beverages, fumigants, pesticides, disinfectants, vitamins, etc. In this form the additives are well preserved from undesirable external factors, can be easily transported, stored and metered, do not deteriorate packings or volatilize. The additives can be liberated instantaneously by dissolving or melting the polymer particles or by crushing them by external pressure.

If the polymer is hydrophilic the additives can diffuse from the swelled particles gradually. Thus, the products of the invention can be also used for sustained release of drugs and similar, for long time sterilization of aqueous liquids etc.

Solids or liquids immiscible with the polymer solution can be incorporated by dispersing them first into the polymer solution, whereafter the emulsion is dispersed, as a whole, into the dispersing medium and together therewith coagulated. In another embodiment, the additive is dissolved in the polymer solvent together with the polymer, the solution dispersed and the emulsion coagulated so that the additive coagulates or precipitates simultaneously with the polymer and forms therewith a solid solution or dispersion. In a similar way, liquids miscible with the polymer solvent and also additives of polymeric nature can be incorporated in the beads. The additives have a very large contact surface with the coagulated polymer. If the polymer is swellable e.g. in water, the swelling agent can diffuse into the additive. Then, if the additive is soluble, it can be gradually eluted into the environment and exert there its activity. If the additive is insoluble in the swelling agent, it can act as catalyst or sorbent. As the particles of the coprecipitated additive are very fine, their active surface is extremely large. In porous beads all minute particles of the additive are readily and equally accessible within seconds after first contact with the swelling agent.

If a liquid volatile additive is either dissolved or finely dispersed in the polymer beads after finished coagulation, the beads can be foamed by heating above the boiling point of the additive and simultaneously above the glass transition point of the polymer, as in the known case of foamed polystyrene. In a closed space the beads can be coalesced to a foamed molding.

Active additives such as catalysts, enzymes and similar can be, if desired, covalently bonded to the polymer, especially to the surface of pores, using known agents and reactions. High molecular enzymes can be simply caged in closed or semi-closed pores, provided that the molecules of the substances are to be treated are sufficiently small to penetrate through the swelled polymer. The adhesiveness of enzymes and other biologically active substances can be increased, if the polymer contains hydrophobic or lyophilic small regions in addition to of hydrophilic ones on its surface.

It is also possible to introduce into the surface layer of the porous beads reactive groups such as carboxylic, sulfonic, sulfurric, amino- or quarternary aminogroups, serving either as ion exchanging means or for covalent binding of other active substances. Various active substances such as enzymes etc. can be incorporated in the polymer also prior to its transformation into swellable or macroporous beads, the present process involving only physical transformations, without chemical reactions which could deteriorate sensitive enzymes or other biologically active substances. If the binding of various active substances onto the polymer is carried out in solution, there is a much broader choice of binding methods in comparison with the usual treatment of the pore surface, and the effectiveness of the reactions is higher.

If desired, transformations of functional groups or binding of further substances and groups onto the polymer can be also realized during the coagulation step. In this case the substances can be bound onto the polymer more effectively than in the usual surface treatment.

The process of the invention can be made continuous so that a polymer solution is fed into a stirred equipped reactor together with a emulsion medium, and the dispersion thus obtained is fed into another vessel where it is stirred into an excess of coagulating liquid. The heterogeneous mixture of beads, dispersing medium and coagulant mixed with the polymer solvent is separated e.g. by filtration, sedimentation and centrifuging, the solution of the solvent with the coagulant being further separated e.g. by rectification, reverse osmosis or other methods, suitable for the compounds in question.

The main advantage of continuous manufacture of beads is better control of size and its distribution as well as porosity. High economy is obtained by the high rate of the physical processes in comparison with e.g. suspension polymerization: At high rates of flow through the equipment the output is very high.

The invention relates to the manufacture of spherical particles from soluble, i.e. non-crosslinked polymers. This does not mean, however, that the product itself must be non-crosslinked since the beads can be crosslinked subsequently in known manner, using at least bifunctional reactive compounds capable of reaction with side-groups of the polymer. Such crosslinking can be carried out preferably during the coagulation, the crosslinking agents being dissolved in the coagulating liquid. Another possibility is to include crosslinking agents in the polymer solution, or also in the dispersing medium from which they are extracted into the droplets of the polymer solution, and to start the crosslinking either in the coagulating bath - e.g. by adding thereto a suitable acid or base or a catalyst, or simply by heating the coagulating bath or the isolated beads. As cross linking agents e.g. various aldehydes can be used, such as formaldehyde, acetaldehyde, benzaldehyde, glyoxal or substances liberating aldehydes during the reaction, such as hexamethylene tetramine. Further utilizable crosslinking agents are di- and polyisocyanates such as hexamethylene diisocyanate or toluylene triisocyanate, di-expoxides, di- and polycarboxylic acids and their reactive derivatives such as halides or anhydrides etc. If a reactive group has been bound with the polymer previously, e.g. epoxide or acylhalide group, the crosslinking may be effectuated using a bifunctional or polyfunctional reactant such as a polyol, polycarboxylic acid, polyamine etc.

When the polymer contains vinylic side-groups or polymerizable double bonds in the main chain, the crosslinking can be effectuated using a suitable monomer, insoluble in the dispersing medium as well as in the coagulating liquid. Such monomer can be also combined with the finished beads. A suitable initiator of polymerization such as dibenzoyl peroxide can be added simultaneously with the monomer and the polymerization is started by heating, preferably in absence of molecular oxygen. Double bond-containing polymers can be crosslinked also by other usual means such as the use of peroxides, sulphur etc.

The invention is further illustrated by the following non-limitative Examples, wherein all parts (p) and percentages are by weight if not stated otherwise.

EXAMPLE 1

Polyacrylonitrile, average molecular weight 550,000, prepared by usual precipitation polymerization, was dissolved in dimethyl sulfoxide to a 5% solution. 5 p of this solution were then dispersed in 25 p of paraffin oil. After 2 minutes of stirring at 250 r.p.m. the emulsion was poured in a thin stream into 25 p of water at 15° C while stirring. After 5 minutes the stirring was discontinued and after a while a layer of spherical beads, average diameter 0.2 mm sedimented on the bottom and could be easily separated from the two liquid phases. The polymer phase took 40% of the volume, the rest was microscopic voids.

EXAMPLE 2

The emulsion from the Example 1 was poured, while stirring intensively, into 100 p of water heated to 60° C. This time the beads possessed a larger diameter of 0.5 mm and the volume of pores amounted to 98% and that of the polymer 2% only.

EXAMPLE 3

The emulsion from Example 1 was poured, while intensively stirring, into 50 p. of a 5% aqueous sodium hydroxide solution at 20° C. After 10 minutes the stirring was discontinued and the sedimented beads washed. The porous beads were colored yellowish-orange, insoluble and contained a high amount of carboxylic groups which could be used either in ion exchange or for binding active substances such as drugs or enzymes, using known agents such as carbodiimides.

EXAMPLE 4

The emulsion from Example 1 was slowly poured while stirring into 25 p of a 50% aqueous dimethyl sulfoxide solution, cooled to 0°C. 100 p of water were then added gradually while stirring. The beads obtained in the above described way, thoroughly washed in water, were hard, transparent, non-macroporous. Their average size was 0.03 mm.

EXAMPLE 5

20 p of acrylonitrile were dissolved in 80 p of 65% nitric acid. 0.1 p of urea, 0.8 p of ammonium persulfate, 0.2 p acetylacetone and 0.03 p of ferric chloride were dissolved in the monomer solution and the whole was left to polymerize at 15° C while cooling externally with tap water. After 22 hours the conversion of polymerization amounted to 93%. After a further 70 hours at the same temperature the polymer was partially hydrolyzed, 40% of the nitrile groups being transformed to predominating amide groups and a small portion of carboxylic groups. The viscous copolymer solution was thoroughly mixed, under reduced pressure, with a mixture of 50 p of finely crystalline urea mononitrate and 50 p of 65% nitric acid. The viscous dispersion of crystals was added gradually, while stirring under atmospheric pressure, into 300 p of a solution of atactic polypropylene in gasoline, viscosity 310 cP. After 20 minutes of stirring the emulsion was dispersed in 500 p of water, and after 15 minutes of stirring the sedimented beads were separated and washed in an excess of warm water, so that the crystals of urea nitrate were dissolved. The spherical beads having an average size of 4 mm contained comparatively large pores. The polymer was highly swellable in water, strong and elastic. It contained reactive amide and carboxylic groups making possible permanent binding of biologically active compounds, even such with high molecular weight. The large pores made possible splitting of high molecular compounds such as proteins or polysaccharides by the respective enzymes.

EXAMPLE 6

8 p of non-crosslinked poly(2-hydroxyethyl methacrylate), prepared by polymerization of commercial grade 2-hydroxyethyl methacrylate according to the U.S. Pat. No. 3,575,946 were dissolved in 100 p of ethylene glycol together with 4 p of monomeric 2-hydroxyethyl methacrylate (containing 5% of the ethyleneglycol dimethacrylate), 0.01 p of cumene hydroperoxide and 8 p of dibutyl ether. The solution was dispersed in 2000 p of n-heptane and the emulsion poured while stirring into 5000 p of an almost saturated sodium chloride solution. The stirring was discontinued and the beads, separated by sedimentation and filtration, were heated for one hour under nitrogen to 105° C and thereafter thoroughly washed in hot distilled water. The crosslinked beads of finely porous 2-hydroxyethyl methacrylate polymer could be used either as a molecular sieve or as a carrier of biologically active substances, sorbed or permanently bound using free hydroxylic groups of the polymer.

EXAMPLE 7

10 p of a methyl methacrylate/vinyl pyrrolidone copolymer (95:5) were dissolved in 120 p of 1,2-dichloroethane and the solution dispersed in 500 p of glycerol. The emulsion was poured while stirring into 2000 p of light gasoline. The separated non-porous beads were washed, dried, put into a fritted disc funnel and rinsed thereon with a 100° C hot mixture of 96% sulfuric acid and glycerol (9:1). Then the beads were thoroughly washed with water, with a 1% aqueous sodium bicarbonate solution and again with water. The non-porous beads possessed a highly hydrophilic surface.

What we claim is:

1. A method of forming a polymeric material into spherical particles or beads, which comprises providing a solution of the polymeric material in a solvent that dissolves the polymeric material without any chemical transformation of the latter; dispersing the resulting polymeric material solution in a liquid dispersing medium that is a non-solvent for the polymeric material and is immiscible with the solvent, the volume ratio of the resulting dispersed phase to the dispersing medium varying from 1:1 to 30:1, the viscosity of the dispersing medium being no more than about one order less than the viscosity of the dispersed phase; adding the resulting emulsion with stirring into an excess of a coagulating liquid that coagulates the polymeric material without any chemical transformation of the latter and that is a non-solvent for the polymeric material, is miscible with the solvent, and is immiscible with the dispersing medium; whereupon the mixture is transformed directly into a three phase system of coagulated polymer, the coagulating liquid and the dispersing medium, and thereafter separating the liquid phases and resulting coagulated polymeric material particles or beads.

2. A method according to claim 1, in which the volume ratio of the dispersed phase to the dispersing medium ranges from 2:1 to 15:1.

3. A method according to claim 1, in which the polymeric material solution includes a liquid or solid additive that is dissolved or dispersed in such solution and that is insoluble in the dispersing medium and the coagulating liquid, such additive being incorporated in the resulting coagulated polymeric material particles or beads.

4. A method according to claim 3, which includes removing the additive from the coagulated polymeric material particles or beads.

5. A method according to claim 3, in which the dissolved or dispersed additive is such as to be coagulated by the coagulating liquid together with the polymeric material.

6. A method according to claim 5, which includes removing the additive from the coagulated polymeric material particles or beads.

7. A method according to claim 1, in which the polymeric material solution includes a solid additive that is dissolved or dispersed in such solution and that is insoluble in the dispersing medium but soluble in the coagulating liquid.

8. A method according to claim 1, in which the coagulating mixture includes a substance that reacts with the coagulated polymeric material to provide the latter with additional or new side groups.

9. A method according to claim 1, in which the coagulating liquid includes a minor proportion of the polymeric material solvent.

10. A method according to claim 9, which includes gradually adding further coagulating liquid to the coagulating mixture during the coagulation of the polymeric material.

11. A method according to claim 1, which includes cross-linking the polymeric material during or after coagulation of the same.

12. A method according to claim 1, which is carried out on a continuous basis.

* * * * *